United States Patent [19]
Sato et al.

[11] Patent Number: 5,242,371
[45] Date of Patent: Sep. 7, 1993

[54] APPARATUS FOR CENTRIFUGALLY SEPARATING A SAMPLE

[75] Inventors: Takeshi Sato; Fujiya Takahata, Katsuta, both of Japan

[73] Assignee: Hitachi, Ltd., Tokyo, Japan

[21] Appl. No.: 662,104

[22] Filed: Feb. 28, 1991

[30] Foreign Application Priority Data

Mar. 3, 1990 [JP] Japan .................. 2-52198

[51] Int. Cl.$^5$ .................. B04B 5/00; B04B 15/00
[52] U.S. Cl. ...................... 494/16; 210/85; 422/72; 436/45; 494/10
[58] Field of Search .............. 494/7, 10, 16, 19, 20, 494/31, 33, 34, 47, 85; 422/63, 65, 67, 72; 436/45, 177; 210/360.1, 380.3, 781, 85, 380.1

[56] References Cited

U.S. PATENT DOCUMENTS

| 3,151,073 | 9/1964 | Anthon | 494/47 X |
| 3,635,394 | 1/1972 | Natelson | 494/7 |
| 3,722,790 | 3/1973 | Natelson | 494/31 X |
| 4,927,545 | 5/1990 | Roginski | 494/10 X |

FOREIGN PATENT DOCUMENTS 154662 9/1983 Japan .
236966 10/1988 Japan .

Primary Examiner—Harvey C. Hornsby
Assistant Examiner—Charles Cooley
Attorney, Agent, or Firm—Fay, Sharpe, Beall, Fagan, Minnich & McKee

[57] ABSTRACT

A shaft for centrifugally separating a sample includes a first shaft element having a first end taper portion and a middle straight portion, and a second shaft element having a second end taper portion. The first shaft element and the second shaft element are coupled and rotate in opposite directions. An adapter having a ring is mounted on the rotating first taper portion of the shaft by the ring. The adapter receives a sample tube and the adapter and the sample tube are transported forward on the first end taper portion of the shaft. The adapter and the sample tube are sent to the middle straight portion of the shaft and the sample is centrifugally separated in the middle straight portion of the shaft. The adapter and the sample tube are sent to the second taper portion of the shaft and disengaged from the second end taper portion of the shaft. The adapter and the sample tube are automatically mounted on the shaft, and the sample is centrifugally separated on the shaft, after which the adapter and the sample tube are automatically disengaged from the shaft.

14 Claims, 5 Drawing Sheets

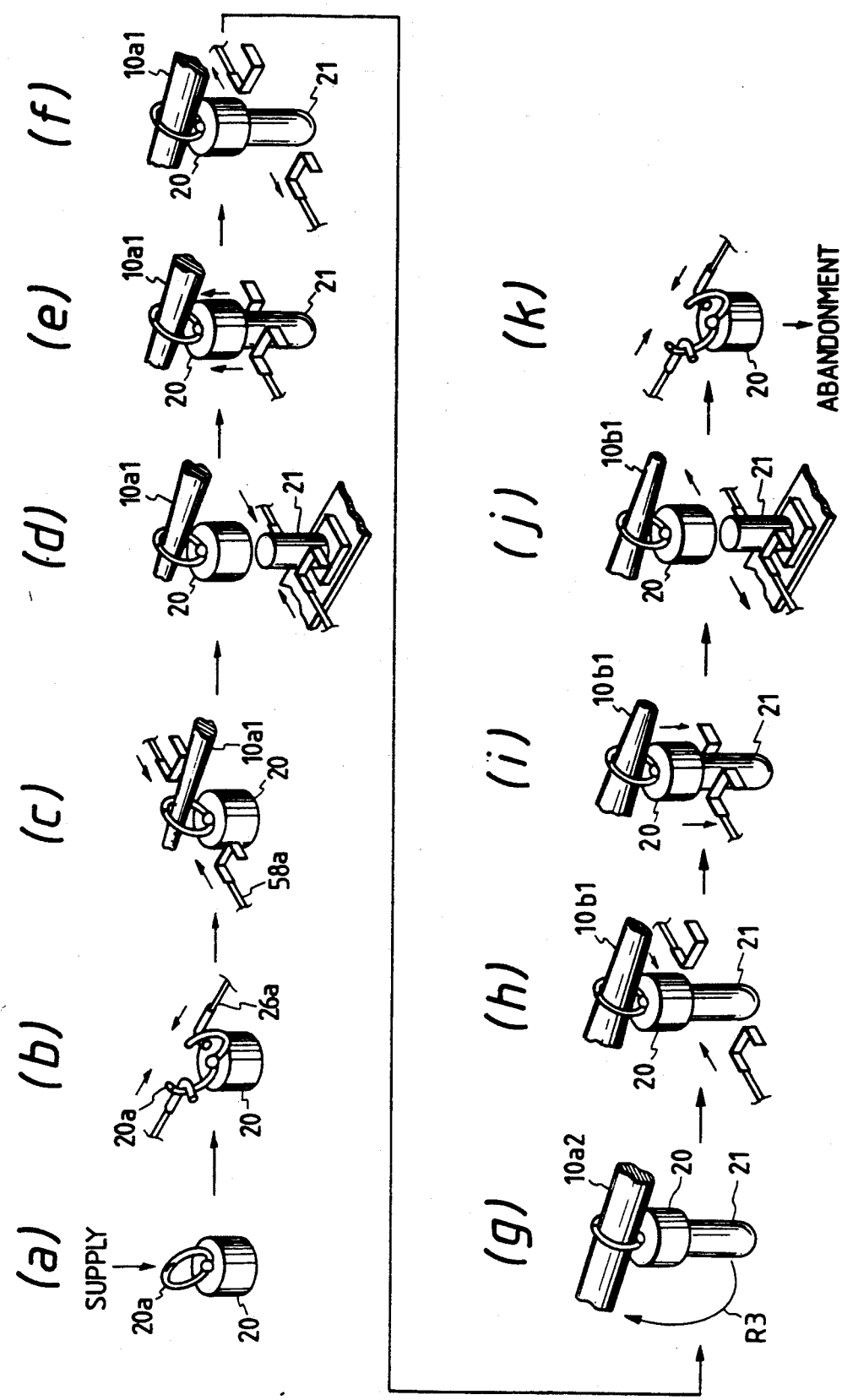

APPARATUS FOR CENTRIFUGALLY SEPARATING A SAMPLE

BACKGROUND OF THE INVENTION

The present invention relates to a method and an apparatus for centrifugally separating a sample for use in a sample centrifugal separation analysis system.

More particularly, the present invention relates to a method for centrifugally separating a sample and an apparatus for the same for use in a sample centrifugal separation analysis system such as in a clinical inspection (biochemical analysis) field, in which a centrifugal separation section for the sample is carried out automatically by employing a rotative centrifugal separation shaft.

In the present invention, an adapter having a sample tube is installed on the sample centrifugal separation shaft, and the adapter is transported from the sample centrifugal separation section to the sample analysis (test) section by the rotation of the centrifugal separation shaft. In this sample centrifugal separation section, the sample is centrifugally separated.

The method and the apparatus for centrifugally separating the sample is applicable to the sample such as blood, blood serum, and urine in a biochemical field.

In a conventional sample centrifugal separation analysis system such as in a clinical inspection field, from the standpoints of high treatment efficiency for a number of specimens (samples) and an high safety for an inflection prevention of an inspector, it is desirable to carry out automatically a series of processes.

Such a series of processes are a sample tube transportation process after a receipt of the sample tube, a pre-treatment process including a centrifugal separation process for the sample, an analysis treatment for the sample, and a data treatment process for analyzing data for the sample.

Within the above stated various processes in the conventional sample centrifugal separation analysis system, an automated operation for the centrifugal separation process for the sample is delayed extremely. In general, the sample tube receiving the sample therein is transported to the sample centrifugal separation section through a manual working operation, and after the finish of the centrifugal separation for the sample in the centrifugal separation section, the sample tube is transported to a next sample analysis (test) section, and at this time the mounting and the disengagement for the sample tube to the holder of the centrifugal separation apparatus is carried out also through a manual working operation.

Recently, for solving the above stated manual working operation in the conventional sample centrifugal separation analysis system, for example as disclosed in Japanese Patent Laid-Open No. 154662/1983, a sample centrifugal separation apparatus is installed in an automatic analysis system, and includes automation for the mounting and the disengagement of the sample tube to the sample centrifugal separator, and automation for aliquotting the centrifugally separated sample.

Further, for example as disclosed in Japanese Patent Laid-Open No. 236966/1988, in a transportation process for the sample tube, an automation technique for a pre-treatment process an analysis employs not the centrifugal separation, but a plane membrane system separation for the sample.

Namely, in the former prior art, the sample centrifugal separation apparatus comprises a rotative vertical shaft, a motor for driving the rotative shaft, a horizontal rotor means disposed on the upper portion of the rotative shaft, and a holder for holding a sample tube. The holder is mounted on a tip of the rotor means and is disposed separately parallel to the rotative shaft. The sample in the sample tube is centrifugally separated by the rotation of the holder.

In this kind of centrifugal separation system for the sample shown in the former prior art, in the automation technique in which the centrifugal separation for the sample is employed as the pre-treatment process, further carrying consideration is paid to carried out automatically the mounting and the disengagement for the sample tube to the sample centrifugal separator through the holder.

However, since the holder of the sample centrifugal separator turns and displaces around the rotative shaft, in a case that the sample tube is mounted to and is disengagement from the holder, it is necessary to stop the sample centrifugal separator and to stop the holder each every time.

Further, in the latter prior art, the pre-treatment process and the sample analysis (test) process are carried out automatically through a belt conveyer means. A plane membrane system automatic blood plasma separation apparatus is employed as the pre-treatment apparatus. The sample in the latter prior art is not separated centrifugally.

Even though the automation technique for the centrifugal separation for the sample is contrived in the conventional sample centrifugal separation analysis system, the centrifugal separation for the sample stops intermittently during the replacement of the sample tube at the sample centrifugal separation section. Accordingly, there are points to be improved for the realization of a rapid automatic analysis treatment for the sample in the conventional sample centrifugal separation analysis system.

SUMMARY OF THE INVENTION

An object of the present invention is to provide a sample centrifugal separation method and a sample centrifugal separation apparatus for use in a sample centrifugal separation analysis system wherein the treatment efficiency for a sample in an automatic analysis system (test) can be heightened.

Another object of the present invention is to provide a sample centrifugal separation method and a sample centrifugal separation apparatus, for use in a sample centrifugal separation analysis system, which can be carried out automatically without a stop motion in a sample centrifugal separation section.

A further object of the present invention is to provide a sample centrifugal separation method and a sample centrifugal separation apparatus for use in a sample centrifugal separation analysis system, wherein a continuous pre-treatment process or a continuous centrifugal separation process for a sample can be carried out automatically.

A further object of the present invention is to provide a sample centrifugal separation method and a sample centrifugal separation apparatus for use in a sample centrifugal separation analysis system, wherein a sample tube is set automatically in sequence to a sample centrifugal separation apparatus.

In accordance with the present invention, a method for centrifugally separating a sample uses a centrifugal separation shaft, in a rotating state.

The sample centrifugal separation method comprises the steps of mounting an adapter having an adapter ring on the centrifugal separation shaft by fitting the adapter ring onto a first end shaft portion of the centrifugal separation shaft; combining the adapter and a sample tube for receiving the sample therein; transporting and rotating a combination body comprised of the adapter and the sample tube to a second end shaft portion of the centrifugal separation shaft by giving an axial direction propelling force with the adapter ring; disengaging the adapter and the sample tube from the second end shaft portion of the centrifugal separation shaft; and releasing the combination body comprised of the adapter and the sample tube.

In accordance with the present invention, an apparatus for centrifugally separating a sample comprises an adapter having an adapter ring for mounting a sample tube, the adapter ring having an opening state and a closing state at an upper portion; a centrifugal separation shaft being rotated by a drive means, the centrifugal separation shaft comprising a first end shaft portion, a middle shaft portion and a second end shaft portion; a diameter dimension of the middle shaft portion of the centrifugal separation shaft being set larger than respective diameter dimension of the first end shaft portion and the second end shaft portion of the centrifugal separation shaft; the respective diameter dimensions of the first end shaft portion and the second end shaft portion of the centrifugal separation shaft being set to be fitted loosely into the adapter ring; the diameter dimension of the middle shaft portion of the centrifugal separation shaft being set to be fitted closely into the adapter ring, the adapter and the sample tube being rotated in company with the centrifugal separation shaft at a position of the middle shaft portion of the centrifugal separation shaft; an adapter mounting mechanism for mounting the adapter ring on the first end shaft portion of the centrifugal separation shaft from a radial direction; an adapter and sample tube combination mechanism for combining the adapter and the sample tube on the centrifugal separation shaft; and adapter and sample tube combination body propelling mechanism for propelling a combination body comprised of the adapter and the sample tube from the first end shaft portion to the second end shaft portion of the centrifugal separation shaft by giving an axial direction propelling force with the adapter ring; an adapter disengagement mechanism for disengaging the adapter ring from the second end shaft portion of the centrifugal separation shaft toward the radial direction; and an adapter and sample tube combination body release mechanism for releasing the combination body comprised of the adapter and the sample tube from the second end shaft portion of the centrifugal separation shaft.

In accordance with the present invention, an apparatus for centrifugally separating a sample comprises an adapter having an adapter ring for mounting a sample tube, the adapter ring having an opening state and a closing state at an upper portion; a centrifugal separation shaft being rotated by a drive means, the centrifugal separation shaft comprising a first end shaft portion, a middle shaft portion and a second end shaft portion; a diameter dimension of the middle shaft portion of the centrifugal separation shaft being set larger than the respective diameters of the first end shaft portion and the second end shaft portion of the centrifugal separation shaft; the respective diameter dimensions of the first end shaft portion and the second end shaft portion of the centrifugal separation shaft being set to be fitted loosely into the adapter ring; the diameter dimension of the middle shaft portion of the centrifugal separation shaft being set to be fitted closely into the adapter ring, the adapter and the sample tube being rotated in company with the centrifugal separation shaft at a position of the middle shaft portion of the centrifugal separation shaft; an adapter mounting mechanism for mounting the adapter ring on the first end shaft portion of the centrifugal separation shaft from a radial direction, the adapter mounting mechanism having a function for opening and closing the adapter ring and a function for positioning the adapter ring against the first end shaft portion of the centrifugal separation shaft; an adapter and sample tube combination mechanism for combining the adapter and the sample tube on the centrifugal separation shaft, the adapter and sample tube combination mechanism setting the adapter and the sample tube in a relative position; an adapter and sample tube combination body propelling mechanism for propelling a combination body comprised of the adapter and the sample tube from the first end shaft portion to the second end shaft portion of the centrifugal separation shaft by giving an axial direction propelling force with the adapter ring, the adapter and sample tube combination body propelling mechanism giving the propelling force against the adapter ring to avoid an collision between the adapter ring disposed on the centrifugal separation shaft and the combination body comprised of the adapter and the sample tube; a rotation displacement mechanism for displacing at least a part of the adapter and sample tube combination body propelling mechanism during a return motion of the adapter and sample tube combination body propelling mechanism to avoid a collision between the adapter and sample tube combination body propelling mechanism and each of the adapter, the adapter ring and the sample tube disposed respectively on the centrifugal separation shaft; an adapter disengagement mechanism for disengaging the adapter ring from the second end shaft portion of the centrifugal separation shaft toward the radial direction, the adapter disengagement mechanism having a function for opening and closing the adapter ring and a function for positioning the adapter ring against the second end shaft portion of the centrifugal separation shaft; and an adapter and sample tube combination body release mechanism for releasing the combination body comprised of the adapter and the sample tube from the second end shaft portion of the centrifugal separation shaft, the adapter and sample tube combination body release mechanism setting the adapter and the sample tube.

In accordance with the present invention, the centrifugal separation operation for the sample is not stopped intermittently, and the sample tube can mount on and disengage from automatically, in turn, the sample centrifugal separation apparatus.

Accordingly, it is possible to carry out the continuous pre-treatment process for the sample, and it is possible to carry out automatic operation for the sample centrifugal separation analysis system, and the operational efficiency for the sample centrifugal separation analysis system can be heightened.

In the process of mounting the adapter to the first end taper portion of the centrifugal separation shaft, the adapter ring mounted on the adapter is fitted to the first end taper portion of the centrifugal separation shaft through the adapter mounting mechanism. Therefore, it is possible to mount the combination body comprised of the adapter and the sample tube on the centrifugal separation shaft.

In this case, even when the centrifugal separation shaft is in the rotating state, since the outer diameter dimension of the first end taper portion of the centrifugal separation shaft is set smaller than the outer diameter dimension of the adapter ring, and further since the centrifugal separation shaft rotates itself, the setting of the positioning for the adapter ring can be carried out easily with the centrifugal separation shaft.

Accordingly, by fitting the adapter to the first end taper portion of the centrifugal separation shaft from the radial direction or from the axial direction, the adapter can mount easily on the centrifugal separation shaft.

The combination of the adapter and the sample tube can be carried out at the time before the adapter mounting process of the adapter on the centrifugal separation shaft and also can be carried out at the time after the adapter mounting process of the adapter on the centrifugal separation shaft.

The reason why the adapter ring is in the loosely fitting state with the centrifugal separation shaft at the stage the adapter has mounted on the first end taper portion of the centrifugal separation shaft is that, even though the centrifugal separation shaft is in the rotating state, the rotating force of the centrifugal separation shaft is not transmitted to the adapter ring.

Accordingly, the adapter and the sample tube maintain substantially the standstill state against the rotating centrifugal separation shaft, and it is possible to set the positions of the adapter and the adapter ring against the sample tube.

After the adapter mounting process of the adapter to the centrifugal separation shaft has finished, the adapter ring which has been the first end taper portion of the centrifugal separation shaft can receive the propelling force from the adapter and sample tube combination body propelling mechanism.

Then the adapter ring and also the adapter and the sample tube being united respectively to the adapter ring can move toward the middle straight portion of the centrifugal separation shaft. Accordingly, the adapter and the sample tube can enter easily to the adapter and sample tube transportation process.

In the adapter and sample tube transportation process, the inner peripheral portion of the adapter ring fits closely to the outer peripheral portion of the middle straight portion of the centrifugal separation shaft. In company with the rotation of the centrifugal separation shaft, not only the adapter ring and but also the adapter and the sample tube can rotate, whereby the centrifugal separation for the sample can be carried out through the rotating centrifugal separation shaft.

At the same time, the adapter and sample tube combination body propelling mechanism continues to give the axial direction propelling force against the adapter ring so as not to collide the rotating adapter and the rotating sample tube, and the adapter and the sample tube can move toward the second end taper portion of the centrifugal separation shaft.

After that, when not only the adapter ring but also the adapter and the sample tube reach the side of the second end taper portion of the centrifugal separation shaft, the adapter ring is in the loosely fitting state against the rotating centrifugal separation shaft.

The rotation of the centrifugal separation shaft is not transmitted to the adapter ring and thereby the rotation of the adapter ring can stop gradually. Not only the adapter ring and but also the adapter the sample tube are almost at the standstill state, and afterward the adapter and the sample tube can enter the adapter and sample tube combination body release process.

In the adapter and sample tube combination body release process, by pulling out the adapter ring from the radial direction or from the axial direction of the centrifugal separation shaft, the adapter can be removed from the centrifugal separation shaft.

Further the release of the combination body comprised of the adapter and the sample tube can be carried out at the time after the adapter ring is removed from the centrifugal separation shaft and also can be carried out at the time before the adapter ring is removed from the centrifugal separation shaft. When the above stated processes are carried out repeatedly, by rotating the centrifugal separation shaft, the sample tube can be mounted in sequence on the rotating centrifugal separation shaft through the adapter and the adapter ring.

Further, after the centrifugal separation for the sample, by rotating the centrifugal separation shaft, the sample tube can be removed from the rotating centrifugal separation shaft through the adapter and the adapter ring.

Therefore, according to the present invention, there is no intermittent rotation stop of the centrifugal separation shaft during the mounting of the sample tube or during the removal of the sample tube, as for the conventional sample centrifugal separation apparatus.

The samples in a plurality of the sample tubes can be separated centrifugally in sequence and can be transported to the side for the next sample analysis process.

The adapter ring mounted on the adapter adopts an opening and closing system structure. As the adapter mounting mechanism for mounting the adapter to the centrifugal separation shaft, the adapter mounting mechanism carries out the functions of opening and closing the adapter ring and also the function of positioning the adapter ring against the first end taper portion of the centrifugal separation shaft.

Therefore, it is possible to fit the adapter ring into the first end taper portion of the centrifugal separation shaft from the radial direction.

When the adapter and the adapter ring reach the second end taper portion of the centrifugal separation shaft, the adapter and sample tube combination body release mechanism works the reversal motion against the motion of the adapter mounting mechanism. Therefore, the adapter can pull out from the second end taper portion of the centrifugal separation shaft from the radial direction through the adapter ring.

Further, the adapter and sample tube combination body propelling mechanism carries out to give the propelling force against the adapter ring from the first end taper portion to the second end taper portion of the centrifugal separation shaft.

During the return operation of the adapter and sample tube combination body propelling mechanism, the propelling arm rotation mechanism works to displace the propelling arm of the adapter and sample tube combination body propelling mechanism.

The collision between the adapter and sample tube combination body propelling mechanism and each of the adapter and ring, the adapter, the sample tube, disposed respectively on the centrifugal separation shaft, can be avoided. Accordingly, it is possible to carry out the return operation for the adapter and sample tube combination body propelling mechanism without obstacle.

Two sample tube transportation mechanisms are installed on the sample centrifugal separation apparatus, namely the first sample tube transportation mechanism for transporting the sample tube to the centrifugal separation section and the second sample tube transportation mechanism for transporting the sample tube to the sample analysis section from the sample centrifugal separation section.

The centrifugal separation shaft is disposed between the first sample tube transportation mechanism and the second sample tube transportation mechanism. The first sample tube transportation mechanism works in cooperation with the adapter and sample tube combination mechanism.

The sample tube transported in sequence from the side of the sample tube receipt section to the sample centrifugal separation section is combined in just the adapter ring and the adapter and fitted into the rotating centrifugal separation shaft through the adapter ring. Therefore, the centrifugal separation for the sample is carried out through the rotating centrifugal separation shaft.

The sample tube after the finish of the sample centrifugal separation is mounted on the second sample tube transportation mechanism and is transported automatically toward the side of the sample analysis section. The second sample tube transportation mechanism works in cooperation with the adapter and sample tube combination body release mechanism.

BRIEF DESCRIPTION OF THE DRAWINGS

FIG. 6 is an explanatory view showing respective process steps for mounting and disengagement of the adapter and the sample tube employed in the above embodiment of the sample centrifugal separation apparatus according to the present invention, wherein:

Figure 7:
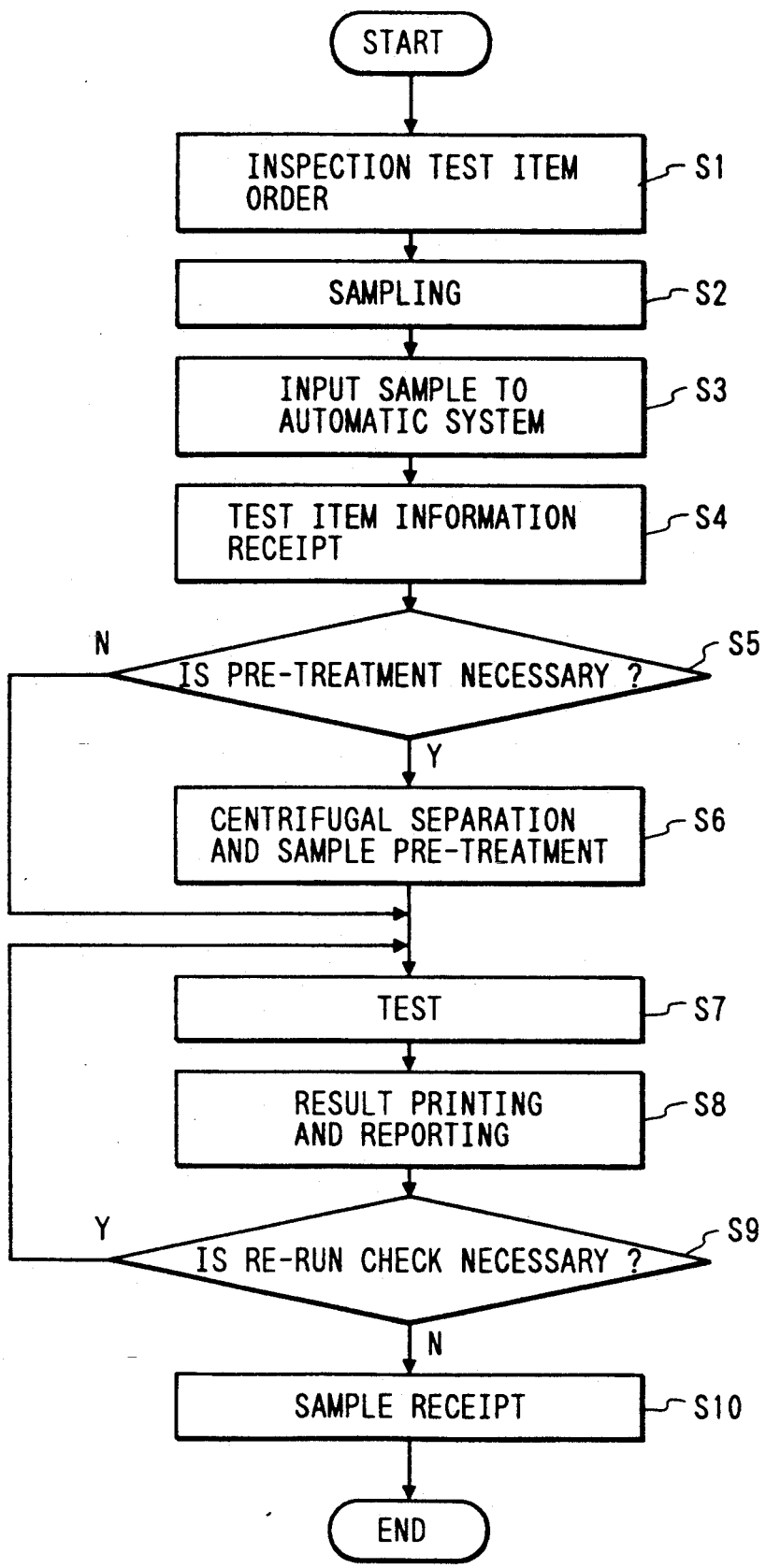

(a) shows a step of supplying an adapter to be mounted;

(b) shows a step of opening an adapter ring of the adapter;

(c) shows a step of closing the adapter ring to fit it onto a first end taper portion of a centrifugal separation shaft;

(d) shows a step of sandwiching a sample tube with a pair of propelling arms;

(e) shows a step of fitting the adapter to the sample tube;

(f) shows a step of releasing the propelling arms from the sample tube;

(g) shows a step of providing the coupled adapter and sample tube at a middle straight portion of a first shaft element of the centrifugal separation shaft;

(h) shows a step of providing the propelling arms to the sample tube at a tapered portion of the centrifugal separation shaft;

(i) shows a step of the propelling arms grasping the sample tube;

(j) shows a step of releasing the sample tube from the adapter; and (k) shows a step of reopening the adapter ring; and FIG. 7 is a flow-chart showing a sample inspection system in which one embodiment of a sample centrifugal separation method according to the present invention is employed.

DESCRIPTION OF THE INVENTION

One embodiment of a sample centrifugal separation method and a sample centrifugal separation apparatus for use in a sample centrifugal separation analysis system according to the present invention will be explained referring to the drawings.

Figure 1:
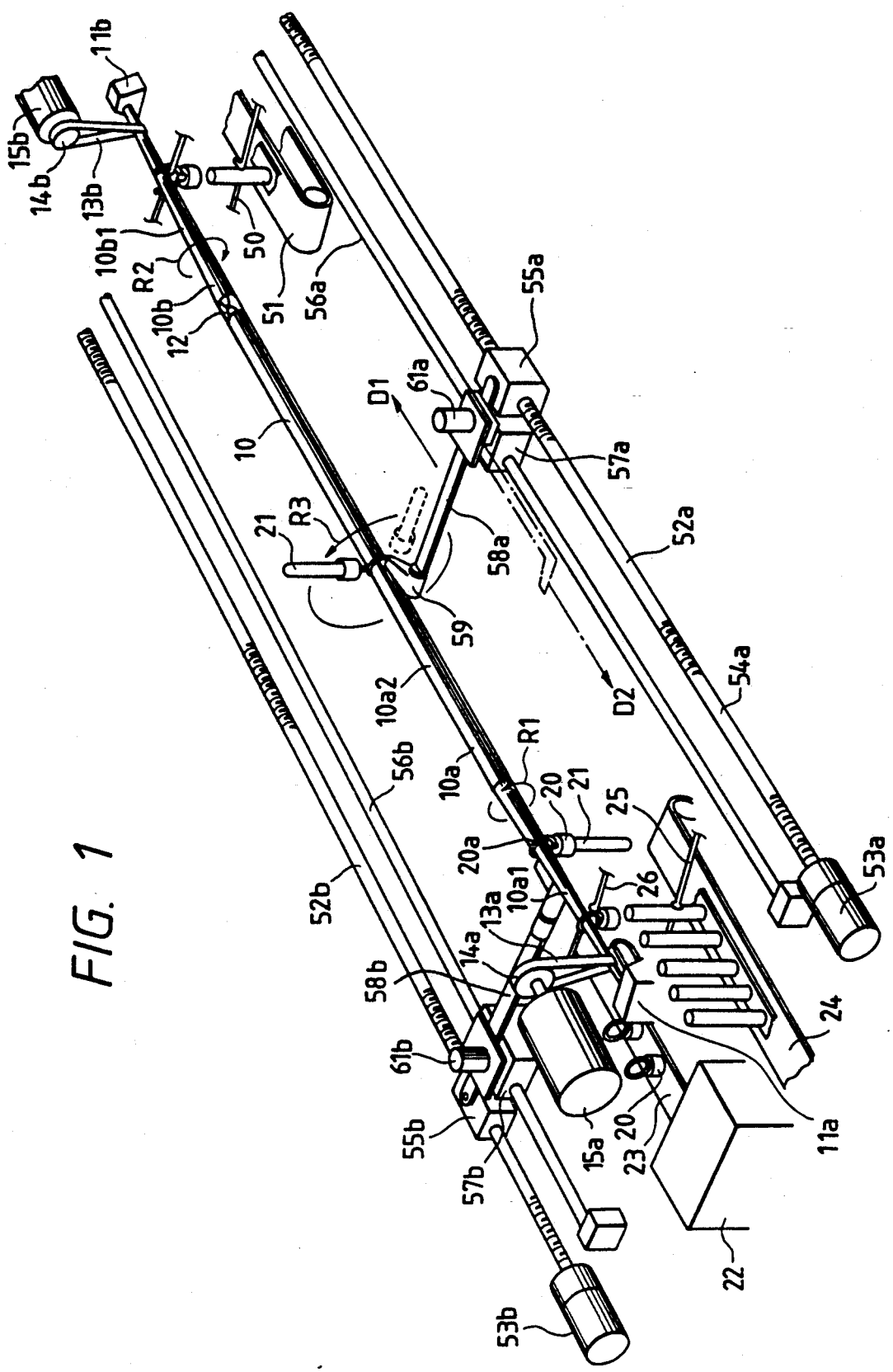
FIG. 1 is a perspective view showing one embodiment of a sample centrifugal separation apparatus according to the present invention.

FIG. 1 is a perspective view showing one embodiment of an outline structure of a sample centrifugal separation apparatus for use in a sample centrifugal separation analysis system according to the present invention.

In FIG. 1, a shaft 10 for centrifugally separating samples is supported through a bearing member at both ends thereof. The bearing member comprises a first bearing member 11a and a second bearing member 11b. The centrifugal separation shaft 10 is disposed horizontally in the sample centrifugal separation apparatus.

The centrifugal separation shaft 10 comprises two shaft element components disposed in an axial direction. This centrifugal separation shaft 10 comprises a first shaft element 10a and a second shaft element 10b. The first shaft element 10a and the second shaft element 10b of the centrifugal separation shaft 10 are combined through a coupling means 12. The first shaft element 10a and the second shaft element 10b of the centrifugal separation shaft 10 rotate relative to each other.

The first shaft element 10a of the centrifugal separation shaft 10 is several times longer than the second shaft element 10b of the centrifugal separation shaft 10. The first shaft element 10a of the centrifugal separation shaft 10 comprises a first end taper portion 10a1 and a middle straight portion 10a2 connected to the first end taper portion 10a1. The second shaft element 10b of the centrifugal separation shaft 10 comprises a second end taper portion 10b1 similar to the first end taper portion 10a1 of the first shaft element 10a.

As stated above, observing the total structure of the centrifugal separation shaft 10, the centrifugal separation shaft 10 has a shaft structure in which both the first end taper portion 10a1 of the first shaft element 10a and the second end taper portion 10b1 of the second shaft element 10b have a taper-shaped outer form structure, and the middle straight portion 10a2 of the first shaft element 10a has a straight-shaped outer form structure.

At the first end taper portion 10a1 of the centrifugal separation shaft 10, a rotational force of a first centrifugal separation shaft drive motor 15a is transmitted through a first rotation force transmission belt member 13a and a first adapter supply pulley member 14a.

Similarly, at one end of the second end taper portion 10b1 of the centrifugal separation shaft 10, a rotational force of a second centrifugal separation shaft drive motor 15b is transmitted through a second rotation force transmission belt member 13b and a second adapter supply pulley member 14b.

A centrifugal separation shaft drive motor comprises the first centrifugal separation shaft drive shaft motor 15a and the second centrifugal separation shaft drive motor 15b. Each of the centrifugal separation shaft drive motors 15a and 15b drives to rotate or stop the centrifugal separation shaft 10. A rotation force transmission belt member comprises the first rotation force transmission belt member 13a and the second rotation force transmission belt member 13b. An adapter supply pulley member comprises the first adapter supply pulley member 14a and the second adapter supply pulley member 14b.

The first shaft element 10a and the second shaft element 10b of the centrifugal separation shaft 10 rotate in opposite directions to each other according to the drive of the first centrifugal separation shaft drive motor 15a and the second centrifugal separation shaft drive motor 15b, respectively.

Figure 3A:
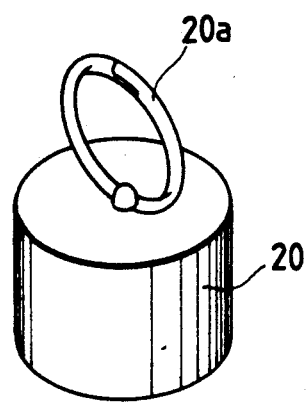
FIG. 3A is a perspective view showing the adapter having the adapter ring in a closing state.
Figure 3B:
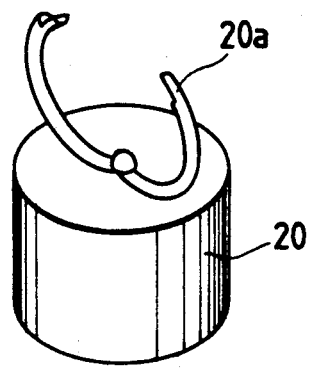
FIG. 3B is a perspective view showing the adapter having the adapter ring in an opening state.

An adapter 20 serves both a cap function for capping a sample tube 21 (specimen tube) and a holder function for holding the sample tube 21. An adapter ring 20a is attached to a top portion of the adapter 20. The adapter ring 20a can open and close itself as shown in FIG. 3A and FIG. 3B.

An inner diameter of the adapter ring 20a is set sufficiently larger than each of a maximum outer diameter of the first end taper portion 10a1 and a maximum outer diameter of the second end taper portion 10b1 of the centrifugal separation shaft 10. Further, the inner diameter of the adapter ring 20a is set substantially equal to an outer diameter of the middle straight portion 10a2 of the centrifugal separation shaft 10.

Namely, when the adapter ring 20a is put into at a position of the first end taper portion 10a1 or the second end taper portion 10b1 of the centrifugal separation shaft 10, since an inner peripheral portion of the adapter ring 20a can fit loosely against the outer peripheral portion of the centrifugal separation shaft 10, accordingly the adapter ring 20a cannot rotate together with the centrifugal separation shaft 10.

On the other hand, when the adapter ring 20a is put into a position of the middle straight portion 10a2 of the centrifugal separation shaft 10, the inner peripheral portion of the adapter ring 20a can fit closely against the outer peripheral portion of the centrifugal separation shaft 10. Therefore, the rotational force of the centrifugal separation shaft 10 is transmitted to the adapter ring 20a, and the sample tube 21 supported by the adapter 20 can rotate together with the centrifugal separation shaft 10.

Figure 2A:
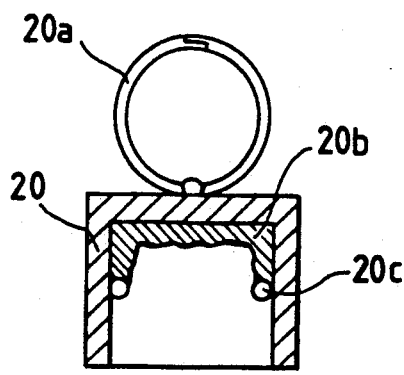
FIG. 2A is a partially cross-sectional view showing an internal structure of an adapter having an adapter ring employed in the above embodiment of the sample centrifugal separation apparatus according to the present invention.
Figure 2B:
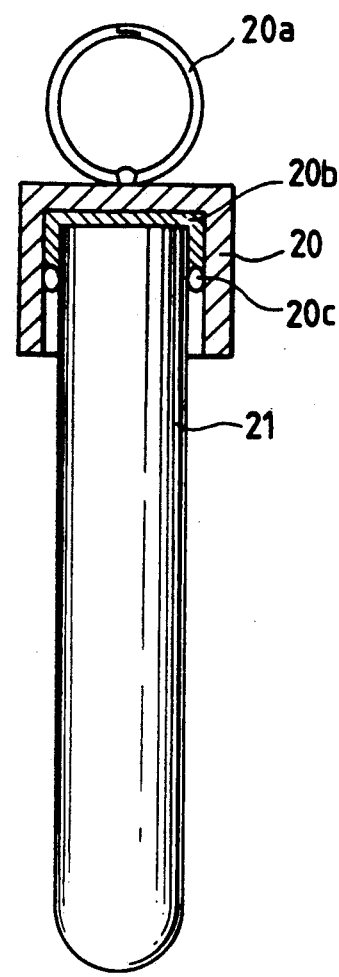
FIG. 2B is a partially cross-sectional view showing a combination body structure between the adapter having the adapter ring and a sample tube.

Further, a cushion member 20b and an O-ring member 20c are mounted on an inner portion of the adapter 20, respectively, as shown in FIG. 2. The cushion member 20b inserted on the adapter 20 is made, for example, of a resin material or a rubber. The cushion member 20b receives an upper opening of the sample tube 21 and can cap the opening of the sample tube 21.

An adapter supply mechanism 22 for supplying the adapter 20 stocks a plurality of adapters 20 within an inner portion thereof. The adapter supply mechanism 22 is set to draw these adapters 20 up to a vicinity of the first end taper portion 10a1 of the centrifugal separation shaft 10 in sequence through the first adapter supply belt member 23.

A first sample tube transportation mechanism 24 transports the sample tube 21 to a sample centrifugal separation section of the centrifugal separation apparatus. The sample tubes 21 which are arranged in one line against the first sample tube transportation mechanism 24 are sent intermittently toward a lower portion of the first end taper portion 10a1 of the centrifugal separation shaft 10 according to the driving force of a pulse motor (not shown).

An adapter mounting mechanism (adapter and sample tube combination mechanism) 25 mounts the adapter 20 to the centrifugal separation shaft 10. In this embodiment of the present invention, the adapter mounting mechanism 25 also combines the adapter 20 and the sample tube 21.

This adapter mounting mechanism 25 comprises a pair of sandwich arms 26 and a three axis direction arm movement mechanism 27 for moving each of the sandwich arms 26 in three directions (X-axis, Y-axis, Z-axis).

Figure 5A:
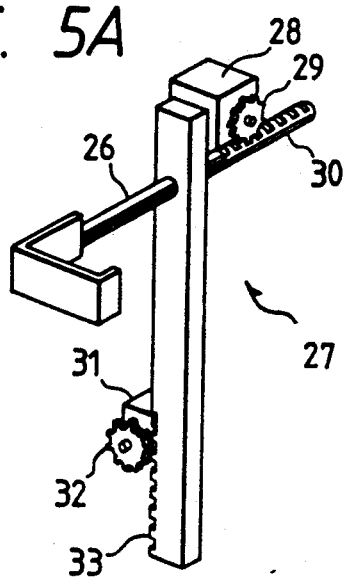
FIG. 5A is a perspective view showing an adapter mounting mechanism structure employed in the above embodiment of the sample centrifugal separation apparatus according to the present invention.
Figure 5B:
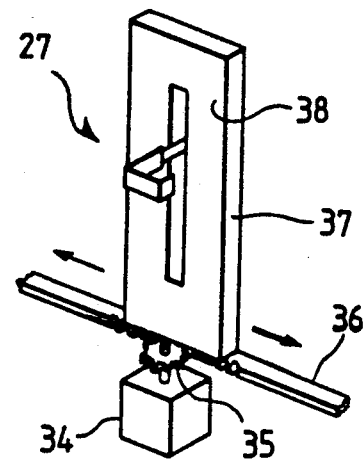
FIG. 5B is a perspective view showing another adapter mounting mechanism structure employed in the above embodiment of the sample centrifugal separation apparatus according to the present invention.

The three axis direction arm movement mechanism 27 comprises an arm movement element for moving the sandwich arm 26 in the X-axis direction, an arm movement element for moving the sandwich arm 26 in the Z-axis direction through a support body 37, and an arm movement element for moving the sandwich arm 26 in the Y-axis direction through a case means 38 for receiving the support body 37, etc., as shown in FIG. 5B.

The arm movement element for moving the sandwich arm 26 in the X-axis direction comprises an X-axis direction pulse motor 28, an X-axis direction gear member 29 and an X-axis direction rack member 30. The arm movement element for moving the sandwich arm 26 in the Z-axis direction comprises a Z-axis direction pulse motor 31, a Z-axis direction gear member 32 and a Z-axis direction rack member 33. The arm movement element for moving the sandwich arm 26 in the Y-axis direction comprises a Y-axis direction pulse motor 34, a Y-axis direction gear member 35 and a Y-axis direction rack member 36.

The adapter mounting mechanism (adapter and sample tube combination mechanism) 25 is disposed at the vicinity of the first end taper portion 10a1 of the centrifugal separation shaft 10 so as to work in close cooperation with the first sample tube transportation mechanism 24.

An adapter disengagement mechanism (adapter and sample tube combination body release mechanism) 50 engages with and disengages from the adapter 20 at a position of the second end taper portion 10b1 of the centrifugal separation shaft 10. This adapter disengagement mechanism 50 also releases the combination body comprising the adapter 20 and the sample tube 21. The adapter disengagement mechanism 50 comprises a pair of the sandwich arms and the three axis direction arm movement mechanism similar to the adapter mounting mechanism 25.

A second sample tube transportation mechanism 51 transports the sample tube 21 from the side of the sample centrifugal separation section to the side of the sample analysis section. The second sample tube transportation mechanism 51 is disposed at a lower portion of the second end taper portion 10b1 of the centrifugal separation shaft 10 so as to work in close cooperation with the adapter disengagement mechanism (adapter and sample tube combination body release mechanism) 50.

An adapter and sample tube combination body propelling mechanism moves the combination body comprising the adapter 20 and the sample tube 21 which is put onto the centrifugal separation shaft 10 in the axial direction. In this embodiment of the present invention, the adapter and sample tube combination body propelling mechanism comprises two propelling mechanisms, namely a first adapter and sample tube combination body propelling mechanism 52a and a second adapter and sample tube combination body propelling mechanism 52b.

The first adapter and sample tube combination body propelling mechanism 52a comprises a first propelling pulse motor 53a, a first screw shaft 54a disposed in the parallel direction of the centrifugal separation shaft 10 and rotated by the first propelling pulse motor 53a, a first movement member 55a that moves in the axial direction by changing the rotational motion of the first screw shaft 54a to a linear reciprocating motion, a first guide shaft 56a, a first propelling arm support body 57a combined integrally with the first movement member 55a and which moves on the first guide shaft 56a, a first propelling arm 58a mounted on the first propelling arm support body 57a, and a first propelling arm rotation mechanism 61a for rotating the first propelling arm 58a.

The second adapter and sample tube combination body propelling mechanism 52b comprises a second propelling pulse motor 53b, a second screw shaft 54b disposed in the parallel direction of the centrifugal separation shaft 10 and rotated by the second propelling pulse motor 53b, a second movement member 55b that moves in the axial direction by changing the rotational motion of the second screw shaft 54b to a linear reciprocating motion, a second guide shaft 56b, a second propelling arm support body 57b combined integrally with the second movement member 55b and which moves on the second guide shaft 56b, a second propelling arm 58b mounted on the second propelling arm support body 57b, and a second propelling arm rotation mechanism 61b for rotating the second propelling arm 58b.

The propelling arm 58a has a pulse motor and a power transmission mechanism. The propelling arm rotation mechanism 61a is set to rotate the propelling arm 58a at a range of about 90°, as shown in a solid line and in a one-dot chain line of FIG. 1.

The propelling arm 58a has a substantially L shape portion at a tip end portion 59 of the propelling arm 58a. When the propelling arm 58a rotates toward a vertical direction with the centrifugal separation shaft 10 as shown in the solid line of FIG. 1, the propelling arm 58a has a sufficient length in which the tip end portion 59 of the propelling arm 58a can contact the centrifugal separation shaft 10.

Figure 4A:
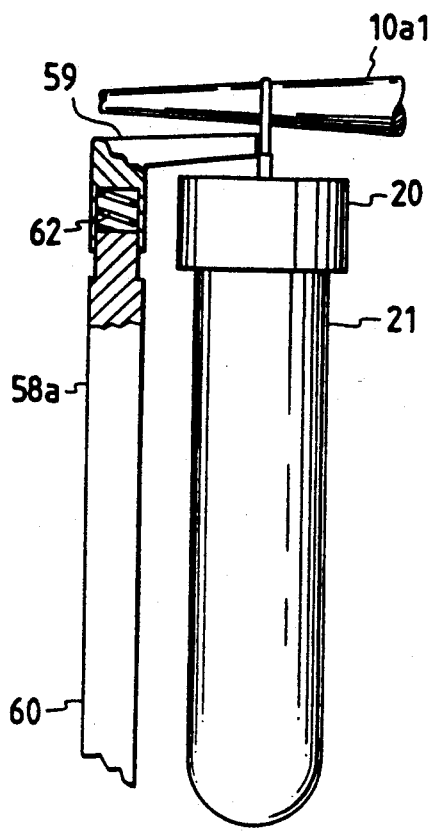
FIG. 4A is a partially cross-sectional explanatory view showing a motion in the first end taper portion on the centrifugal separation shaft of the above embodiment of the sample centrifugal separation apparatus according to the present invention.
Figure 4B:
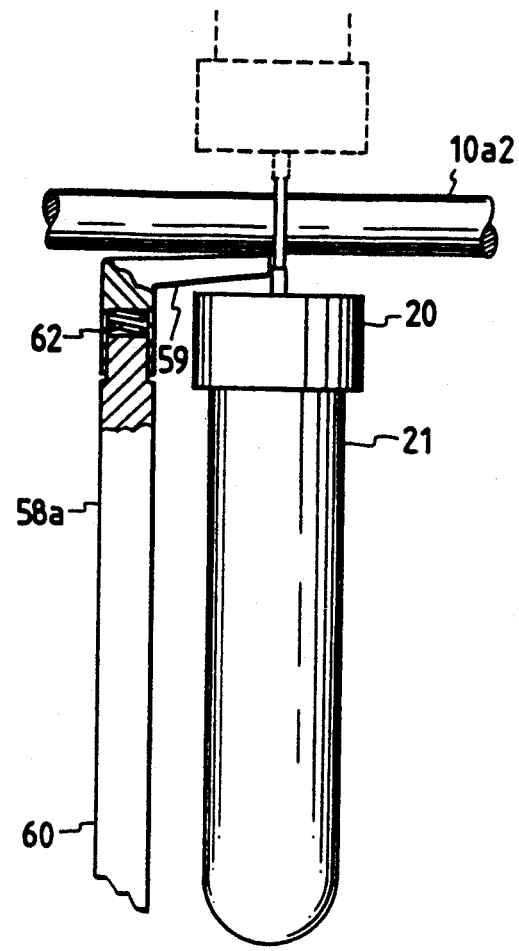
FIG. 4B is a partially cross-sectional explanatory view showing a motion in the middle straight portion on the centrifugal separation shaft of the above embodiment of the sample centrifugal separation apparatus according to the present invention.

Further, the tip end portion 59 of the propelling arm 58a is fitted to insert flexibly into a propelling arm main body 60 of the propelling arm 58a through a spring member 62, as shown in FIGS. 4A and 4B. The reason for making the above propelling arm structure is that the tip end portion 59 of the propelling arm 58a can maintain contact and move in the axial direction, even when the diameter dimension of the centrifugal separation shaft 10 changes against the diameter dimension of the propelling arm 58a in accordance with the variation in the diameter dimension of the centrifugal separation shaft 10.

Further, the propelling arm 58a is set not to collide with the adapter 20 and the sample tube 21, because the tip end portion 59 of the propelling arm 58a can contact an end portion of the adapter ring 20a disposed on the centrifugal separation shaft 10, and the tip end portion 59 of the propelling arm 58a can contact the adapter ring 20a with the substantially L shape portion arm structure.

Next, a series of motions of the embodiment of the sample centrifugal separation apparatus in the sample centrifugal separation analysis system according to the present invention will be explained.

First of all, the various motors are driven and controlled by a control unit (not shown). Such various motors are the drive motor for rotating and stopping the centrifugal separation shaft 10, comprising the first centrifugal separation shaft drive motor 15a and the second centrifugal separation shaft drive motor 15b, the motor for driving the first adapter supply belt member 13a and the second adapter supply belt member 13b, the motor for driving the first sample tube transportation mechanism 15a, the propelling pulse motor for driving the adapter and sample tube combination body propelling mechanism 52a, and comprising the first propelling pulse motor 53a and the second propelling pulse motor 53b, and the motor for driving the second sample tube transportation mechanism 51.

Among these motors, the first end taper portion 10a1 and the second end taper portion 10b1 of the centrifugal separation shaft 10 are controlled to rotate in opposite directions (R1 rotating direction or R2 rotating direction shown in FIG. 1) according to the first centrifugal separation shaft drive motor 15a and the second centrifugal separation shaft drive motor 15b.

Further, the sample tube 21 disposed on the first sample tube transportation mechanism 24 and the adapter 20 disposed on the adapter transportation belt member 23 are transported intermittently in sequence to a predetermined position (the first end taper portion 10a1 of the centrifugal separation shaft 10).

When the adapter 20 reaches the predetermined position, the adapter 20 is mounted by the adapter mounting mechanism 25 in accordance with the following method.

The various processes of the mounting motion and the removal motion for the adapter 20 and the sample tube 21 are shown at (a)–(k) in FIG. 6. The arrows in FIG. 6 show the mounting manner and the removal manner for the adapter 20 and the sample tube 21 in the mounting motion and the removal motion of the process.

The adapter 20 is mounted on the first end taper portion 10a1 of the first shaft element 10a of the centrifugal separation shaft 10 in accordance with the following processes. After a supply process as shown at (a) in FIG. 6 in which the adapter 20 is supplied to the first end taper portion 10a1 of the centrifugal separation shaft 10, the pair of sandwich arms 26 are moved in the X-axis direction or Y-axis direction according to a predetermined motion are passed to the inside portion of the adapter ring 20a.

While maintaining this state, each of the pair of sandwich arms 26 is given respectively an outside direction force and then the adapter ring 20a is opened, as shown at (b) in FIG. 6. In this state, the adapter ring 20a is moved in the Z-axis direction (upper direction) and the adapter ring 20a is fitted onto the first end taper portion 10a1 of the centrifugal separation shaft 10, as shown at (c) in FIG. 6.

Before closing the adapter ring 20a, that the pair of sandwich arms 26a are moved out of contact with the outside portion of the adapter ring 20a. In this state, when the adapter ring 20a is released from the pair of sandwich arms 26a, the adapter ring 20a can close to some degree by its inherent spring force. Accordingly, the adapter ring 20a is prevented from dropping out carelessly from the first end taper portion 10a1 of the centrifugal separation shaft 10.

Next, the adapter ring 20a is given an inside direction force from the outside portion, and then the adapter ring 20a can be closed completely. Therefore, the mounting operation of the adapter 20 is finished. In this mounted state, the adapter ring 20a is fitted loosely at the first end taper portion 10a1 of the centrifugal separation shaft 10. Thus, when the centrifugal separation shaft 10 rotates, the adapter 20 does not rotate.

Next, the pair of propelling arms 26a descend in the Z-axis direction, and the pair of propelling arms 58a are moved in the X-axis direction towards the inside portion, as shown at (d) in FIG. 6. Then the pair of propelling arms 58a sandwich the sample tube 21 which is disposed on the first end taper portion 10a1 of the centrifugal separation shaft 10.

Next, the sample tube 21 is positioned to the adapter 20 and is lifted up, so that the adapter 20 can be fitted to the sample tube 21, as shown at (e) in FIG. 6. Next, the pair of propelling arms 58a release the sample tube 21, as shown at (f) in FIG. 6.

When the adapter 20 and the sample tube 21 are mounted on the first end taper portion 10a1 of the centrifugal separation shaft 10, the first and the second adapter and sample tube combination body propelling mechanisms 52a and 52b move mutually at the vicinity of the mounting position for the adapter 20.

The tip end portion 59 of the propelling arm 58a contacts the adapter ring 20a from the rear side against the advancing direction of the adapter 20, as shown in FIG. 4, and here the first and the second adapter and sample tube combination body propelling mechanisms 52a and 52b move in turn in the direction marked by an arrow D1 (FIG. 1).

In accordance with this move, the propelling arm 58a gives a propelling force against the adapter 20 and the sample tube 21 through the adapter ring 20a, so that the adapter 20 and the sample tube 21 move smoothly along the tapering portion of the first end taper portion 10a1 of the centrifugal separation shaft 10 and reach the middle straight portion 10a2 of the first shaft element 10a of the centrifugal separation shaft 10 as shown at (g) in FIG. 6.

The adapter ring 20a fits closely to the middle straight portion 10a2 of the centrifugal separation shaft 10 and rotates in company with the centrifugal separation shaft 10 in the direction marked by an arrow D2 according to the drive of the first centrifugal separation shaft drive motor 15a. Accordingly, the centrifugal separation for the sample in the sample tube 21 is carried out on the rotating centrifugal separation shaft 10.

In course of the rotation of the adapter 20 and the sample tube 21, namely at the time during which the centrifugal separation for the sample received in the sample tube 21 is carried out, the first and the second adapter and sample tube combination body propelling mechanisms 52a and 52b operate. Since the tip end portion 59 of the propelling arm 58a pushes one end of the adapter ring 20a, the adapter 20 and the sample tube 21 are moved in the direction of an arrow mark D1 and reach the second end taper portion 10b1 of the second shaft element 10b of the centrifugal separation shaft 10.

The adapter 20 and the sample tube 21 rotate reversely in the direction of the arrow mark R2 according to the drive of the second centrifugal separation shaft drive motor 15b. At a portion in which the inner diameter dimension of the adapter ring 20a corresponds substantially to the outer diameter dimension of the second end taper portion 10b1 of the centrifugal separation shaft 10, a strong rotational restraint force operates against the adapter 20 and the sample tube 21.

After the adapter ring 20a reaches the tapering portion of the second end taper portion 10b1 of the centrifugal separation shaft 10, since at this tapering portion the inner diameter dimension of the adapter ring 20a is larger than the outer diameter dimension of the second end taper portion 10b1 of the centrifugal separation shaft 10, the adapter ring 20a becomes loosely fit at the tapering portion of the second end taper portion 10b1 of the centrifugal separation shaft 10. Accordingly, the adapter 20 and the sample tube 21 are maintained substantially still at the second end taper portion 10b1 of the centrifugal separation shaft 10.

When the adapter 20 and the sample tube 21 reach a predetermined position of the second end taper portion 10b1 of the centrifugal separation shaft 10, a reverse command signal is sent to the propelling arm rotation mechanism 61 for driving the propelling arm 58a through the control unit. Then the propelling arm 58a is driven and controlled at a reversal state of 90°. This reversal state of the propelling arm 58a is indicated with the one-dot chain line in FIG. 1.

Further, a control signal is sent to the propelling pulse motor 53a for propelling the adapter and sample tube combination body propelling mechanism 52 to rotate reversely through the control unit, then the movement member 55a is driven and controlled to return back toward the first end taper portion 10a1 of the centrifugal separation shaft 10.

Once adapter 20 and the sample tube 21 reach the predetermined position of the second end taper portion 10b1 of the centrifugal separation shaft 10 the adapter 20 and the sample tube 21 are removed from the second end taper portion 10b1 of the centrifugal separation shaft 10 according to the adapter and sample tube combination body release mechanism 50. Namely, the sample tube 21 is first disengaged from the adapter 20, and then the adapter 20 is removed from the second end taper portion 10b1 of the centrifugal separation shaft 10.

The above stated combination and removal operation for the adapter 20 is carried out according to the processes (h)-(k) shown in FIG. 6. Each of the combination and removal processes for the adapter 20 is indicated with the arrow mark lines.

The removed adapter 20 is abandoned from the centrifugal separation apparatus in the sample centrifugal separation analysis system, and the sample tube 21 is transported to the side of the sample analysis (test) section through the second sample tube transportation mechanism 51.

In this embodiment of the present invention, the continuous centrifugal separation motion for the sample is carried out according to the repetition of the above stated motion.

FIG. 7 is a flow-chart showing a case in which the continuously centrifugal separation apparatus using the above stated embodiment according to the present invention is adapted to the automatic sample analysis system for the sample. This flow-chart is adapted for the sample (specimen) inspection in the clinic biochemical field.

In FIG. 7, in a step S1 the inspection test item order is carried out and in a step S2 the sampling is carried out. The sample is introduced into the automatic system at a step S3 and in a step S4 the test item information for the sample is received.

In a step S5 it is judged whether the pre-treatment for the sample is necessary or not. As a result, when the centrifugal separation for the sample is necessary as the pre-treatment for the sample, the centrifugal separation motion using this embodiment according to the present invention is carried out.

In a step S6 the centrifugal separation and the pre-treatment for the sample are carried out, in a step S7 of the test (sample analysis) the sample is analyzed and in a step S8 the printing and the reporting of the results of the analyzed sample are carried out. In a step S9 it is judged whether the re-run check for the sample is necessary or not. In a step S10 the sample receipt is carried out.

According to the above stated embodiment of the present invention, the following effects can be obtained.

The temporary working interruption at the sample centrifugal separation section in the sample analysis system for the sample, in particularly the stop of the centrifugal separation section in the sample analysis system for the sample, in particularly the stop of the centrifugal separation operation for the sample during the mounting and the removal of the sample tube 21, which is the problem in the conventional separation analysis system for the sample, can be solved.

Accordingly, a good system operation having the continuous centrifugal separation operation in the sample analysis system for the sample can be assured. In particular, in a case that the adapter and sample tube combination body propelling mechanisms 52a and 52b as shown in the embodiment of the present invention are adopted, the efficiency in the system operation having the continuous centrifugal separation operation in the analysis system for the sample can be heightened.

Since the first and the second end taper portions 10a1 and 10b1 of centrifugal separation shaft 10 for centrifugally separating the sample are formed in tapering shapes, not only the movement of the adapter ring 20a but also the movement of the adapter 20 and the sample tube 21 can be carried out smoothly.

The centrifugal separation shaft 10 for centrifugally separating the sample comprises two components, which are the first shaft element 10a and the second shaft element 10b. The first shaft element 10a and the second shaft element 10b of the centrifugal separation shaft 10 are combined to rotate in opposite directions.

At the side of the second shaft element 10b of the centrifugal separation shaft 10, since the rotation can be slowed by braking, the stopping of the sample tube 21 in which the sample has been centrifugally separated can be sped up, whereby the release for the combination body comprised of the adapter 20 and the sample tube 21 can be carried out quickly.

In the above stated embodiment of the present invention, after the adapter 20 is mounted on the first end taper portion 10a1 of the centrifugal separation shaft 10, the combination of the adapter 20 and the sample tube 21 is carried out. However, the combination body comprised of the adapter 20 and the sample tube 21 may be carried out in advance.

Similarly to the release of the combination body comprised of the adapter 20 and the sample tube 21 carried out after the adapter 20 is mounted on the second end taper portion 10b1 of the centrifugal separation shaft 10.

In the above stated embodiment of the present invention, since the centrifugal separation shaft 10 is supported at both tip end portions by two bearing members 11a and 11b, the fitting and the releasing of the adapter ring 20a is carried out from the radial direction of the centrifugal separation shaft 10. However, in a case that the centrifugal separation shaft 10 is supported with a cantilever form structure through only one bearing member, at the side of the tip end of the centrifugal separation shaft 10, the adapter ring 20a can be fit or released from the axial direction of the centrifugal separation shaft 10.

As the drive source for the adapter and sample tube combination body propelling mechanisms 52a and 52b, a reciprocating operation mechanism such as a hydraulic cylinder apparatus may employed, however the kind of the drive for the adapter and sample tube combination body propelling mechanisms 52a and 52b is not restricted.

The centrifugal separation shaft 10 can employ single shaft structure, being not divided. Further, each of the first end taper portion 10a1 and the second end taper portion 10b1 of the centrifugal separation shaft 10 is not required to be made with the complete tapering form structure but can be made with a substantially straight form structure.

We claim:

1. An apparatus for centrifugally separating a sample comprising:
a sample tube;
an adapter for mounting said sample tube, said adapter having an adapter ring, said adapter ring being capable of assuming an opening state and a closing state;
a centrifugal separation shaft being rotated by a drive means, said centrifugal separation shaft comprising a first end shaft portion, a middle shaft portion and a second end shaft portion;
a diameter of said middle shaft portion of said centrifugal separation shaft being set larger than respective diameters of said first end shaft portion and said second end shaft portion of said centrifugal separation shaft;
said respective diameters of said first end shaft portion and said second end shaft portion of said centrifugal separation shaft being arranged so that said adapter ring loosely fits around said respective diameters;

said diameter of said middle shaft portion of said centrifugal separation shaft being arranged so that said adapter ring fits closely around said middle shaft diameter, said adapter and said sample tube thus being rotatable together as a unit with said centrifugal separation shaft at a position of said middle shaft portion of said centrifugal separation shaft;

an adapter mount mechanism for mounting said adapter ring on said first end shaft portion of said centrifugal separation shaft;

an adapter and sample tube combination mechanism for combining said adapter and said sample tube as a unit on said centrifugal separation shaft;

an adapter and sample tube combination body propeller mechanism for propelling the unit comprised of said adapter and said sample tube from said first end shaft portion to said second end shaft portion of said centrifugal separation shaft by giving an axial direction propelling force to said adapter ring;

an adapter and sample tube combination body release mechanism for releasing said sample tube from said adapter; and an adapter disengagement mechanism for disengaging said adapter ring from said second end shaft portion of said centrifugal separation shaft.

2. An apparatus for centrifugally separating a sample according to claim 1, wherein said sample centrifugal separation apparatus comprises further a rotation displacement mechanism for displacing at least a part of said adapter and sample tube combination body propeller mechanism during a reversing operation of said centrifugal separation shaft to avoid a collision between said adapter and sample tube combination body propeller mechanism and any of said adapter, said adapter ring and said sample tube.

3. An apparatus for centrifugally separating a sample according to claim 1, wherein said adapter mount mechanism includes means for opening and closing said adapter ring.

4. An apparatus for centrifugally separating a sample according to claim 1, wherein said adapter mount mechanism includes means for positioning said adapter ring against said first end shaft portion of said centrifugal separation shaft.

5. An apparatus for centrifugally separating a sample according to claim 1, wherein said adapter and sample tube combination mechanism combines said adapter and said sample tube at a time that is one of before and after an adapter mounting process to said centrifugal separation shaft.

6. An apparatus for centrifugally separating a sample according to claim 1, wherein said adapter and sample tube combination body propeller mechanism includes means for exerting said propelling force against said adapter ring to avoid a collision between said adapter ring and said unit of said adapter and said sample tube.

7. An apparatus for centrifugally separating a sample according to claim 1, wherein said adapter disengagement mechanism includes means for opening and closing said adapter ring.

8. An apparatus for centrifugally separating a sample according to claim 1, wherein said adapter and sample tube combination body release mechanism releases said sample tube from said adapter at a time that is one of before and after an adapter release process from said centrifugal separation shaft.

9. An apparatus for centrifugally separating a sample comprising:

a sample tube;

an adapter for mounting said sample tube, said adapter having an adapter ring, and said adapter ring being capable of assuming an opening state and a closing state;

a centrifugal separation shaft being rotated by a drive means, said centrifugal separation shaft comprising a first end shaft portion, a middle shaft portion and a second end shaft portion;

a diameter of said middle shaft portion of said centrifugal separation shaft being set larger than respective diameters of said first end shaft portion and said second end shaft portion of said centrifugal separation shaft;

said respective diameters of said first end shaft portion and said second end shaft portion of said centrifugal separation shaft being arranged so that said adapter ring loosely fits around said respective diameters;

said diameter of said middle shaft portion of said centrifugal separation shaft being arranged so that said adapter ring fits closely around said middle shaft portion, said adapter and said sample tube thus being rotatable together as a unit with said centrifugal separation shaft at a position of said middle shaft portion of said centrifugal separation shaft;

an adapter mount mechanism for mounting said adapter ring on said first end shaft portion of said centrifugal separation shaft, said adapter mount mechanism including means for opening and closing said adapter ring and means for positioning said adapter ring against said first end shaft portion of said centrifugal separation shaft;

an adapter and sample tube combination mechanism for combining said adapter and said sample tube as a unit on said centrifugal separation shaft, said adapter and sample tube combination mechanism combining said adapter and said sample tube;

an adapter and sample tube combination body propeller mechanism for propelling the unit comprised of said adapter and said sample tube from said first end shaft portion to said second end shaft portion of said centrifugal separation shaft by giving an axial direction propelling force to said adapter ring to avoid a collision between said adapter ring and said sample tube;

a rotation displacement mechanism for displacing at least a part of said adapter and sample tube combination body propeller mechanism during a reversing operation of said centrifugal separation shaft to avoid a collision between said adapter and sample tube combination body propeller mechanism and any of said adapter, said adapter ring and said sample tube;

an adapter and sample tube combination body release mechanism for releasing said sample tube from said adapter; and an adapter disengagement mechanism for disengaging said adapter ring from said second end shaft portion of said centrifugal separation shaft, said adapter disengagement mechanism including means for opening and closing said adapter ring.

10. An apparatus for centrifugally separating a sample according to claim 9, wherein
said centrifugal separation shaft includes a first shaft element having said first end shaft portion and said middle shaft portion, and a second shaft element rotatively connected to said first shaft element with respect to said first shaft element, said second shaft element having said second end shaft portion 11. An apparatus for centrifugally separating a sample according to claim 9, wherein
each of said first end shaft portion and said second end shaft portion of said centrifugal separation shaft is formed with a tapering portion that gradually decreases in diameter toward a shaft tip end.

12. An apparatus for centrifugally separating a sample according to claim 9, wherein
said adapter and sample tube combination body propeller mechanism comprises a reciprocating movement mechanism having a movement element and a propelling arm member;
said reciprocating movement mechanism carries out a reciprocating motion over a distance at least corresponding to from said first end shaft portion to said second end shaft portion of said centrifugal separation shaft;
said propelling arm member is connected to said movement element of said reciprocating movement mechanism and contacts one end portion of said adapter ring fitted onto said centrifugal separation shaft to avoid a collision with said combination body; and
said propelling arm member is supported rotatively within a setting range by said rotation displacement mechanism.

13. An apparatus for centrifugally separating a sample according to claim 9, further comprising:
a first transportation mechanism for transporting a plurality of said adapters in sequence to a working position of said adapter mount mechanism;
a second transportation mechanism for transporting a plurality of said sample tubes in sequence to a working position of said adapter and sample tube combination mechanism;
a third transportation mechanism for transporting said adapter being disengaged from said centrifugal separation shaft and being released from the unit of said adapter and said sample tube toward a recovery side with interconnection of said adapter and sample tube combination body release mechanism; and
a fourth transportation mechanism for transporting said sample tube being released from a combination body state of said adapter and said sample tube toward a sample analysis section side.

14. An apparatus for centrifugally separating a sample for use in a sample analysis system in which the sample received in a sample tube is centrifugally separated and the sample is transported to a sample analysis section for automatic sample analysis, said sample centrifugal separation apparatus comprising:
a sample tube;
a number of adapters having an adapter ring for mounting said sample tube;
a sample tube carry-in mechanism for transporting said sample tube to a sample centrifugal separation section;
a sample tube carry-out mechanism for transporting said sample tube from said sample centrifugal separation section to said sample analysis section;
a centrifugal separation shaft being disposed between said sample tube carry-in mechanism and said sample tube carry-out mechanism and being rotated by a drive motor, and said centrifugal separation shaft comprising a first end shaft portion, a middle shaft portion and a second end shaft portion;
a diameter of said middle shaft portion of said centrifugal separation shaft being set larger than respective diameters of said first end shaft portion and said second end shaft portion of said centrifugal separation shaft;
said respective diameters of said first end shaft portion and said second end shaft portion of said centrifugal separation shaft being arranged so that said adapter ring fits loosely around said respective diameters;
said diameter of said middle shaft portion of said centrifugal separation shaft being arranged so that said adapter ring fits closely around said middle shaft portion, said adapter and said sample tube being rotatable together as a unit with said centrifugal separation shaft at a position of said middle shaft portion of said centrifugal separation shaft;
an adapter mount mechanism for mounting said adapter on said centrifugal separation shaft by fitting said adapter ring on said first end portion of said centrifugal separation shaft;
an adapter and sample tube combination mechanism for combining said adapter and said sample tube as a unit on said centrifugal separation shaft;
an adapter and sample tube combination body propeller mechanism for propelling the unit comprised of said adapter and said sample tube from said first end shaft portion to said second end shaft portion of said centrifugal separation by giving an axial direction propelling force to said adapter ring to avoid a collision of said adapter ring and said sample tube, and said adapter and sample tube combination body propeller mechanism having returning means for returning said combination body to said first end shaft portion of said centrifugal separation shaft from said second end shaft portion;
a rotation displacement mechanism for displacing at least a part of said adapter and sample tube combination body propeller mechanism during a reversing operation of said centrifugal separation shaft to avoid a collision between said adapter and sample tube combination body propeller mechanism and any of said adapter, said adapter ring and said sample tube;
an adapter and sample tube combination body release mechanism for releasing said sample tube from said adapter; and
an adapter disengagement mechanism for disengaging said adapter from said centrifugal separation shaft by pulling out said adapter ring from said second end shaft portion of said centrifugal separation shaft;
wherein said adapter and sample tube combination mechanism is interconnected to said sample tube carry-in mechanism, and said adapter and sample tube combination body release mechanism is interconnected to said sample tube carry-out mechanism.

* * * * *